United States Patent [19]

Karcher et al.

[11] Patent Number: 4,967,015
[45] Date of Patent: Oct. 30, 1990

[54] POLYTETRAHYDROFURAN VINYL ETHERS

[75] Inventors: Michael Karcher, Dossenheim; Heinz Eckhardt, Ludwigshafen; Jochem Henkelmann, Bensheim, all of Fed. Rep. of Germany

[73] Assignee: BASF Aktiengesellschaft, Ludwigshafen, Fed. Rep. of Germany

[21] Appl. No.: 422,134

[22] Filed: Oct. 16, 1989

[30] Foreign Application Priority Data

Nov. 4, 1988 [DE] Fed. Rep. of Germany ....... 3837469

[51] Int. Cl.$^5$ .............................................. C07C 43/16
[52] U.S. Cl. ..................................... 568/616; 568/617
[58] Field of Search ................................ 568/616, 617

[56] References Cited

U.S. PATENT DOCUMENTS

| 1,959,927 | 3/1934 | Reppe .................................. 568/616 |
| 2,066,076 | 12/1936 | Reppe et al. . |
| 2,692,256 | 10/1954 | Bauer et al. ......................... 568/616 |
| 2,782,167 | 2/1957 | Tutwiler .............................. 568/616 |
| 3,824,198 | 3/1974 | Smith et al. . |
| 4,751,273 | 6/1988 | Lapin et al. . |

4,766,252 8/1988 Vara et al. .

FOREIGN PATENT DOCUMENTS 66179 5/1982 European Pat. Off. .

OTHER PUBLICATIONS

Journal of Macromolecular Science, Reviews in Macromolecular Chemistry and Physics, C25 (1985), No. 3.

Primary Examiner—Howard T. Mars
Attorney, Agent, or Firm—John H. Shurtleff

[57] ABSTRACT

Polytetrahydrofuran vinyl ethers of the general formula

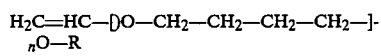

I where R is hydrogen or the CH=CH radical and n is from 2 to 150, are prepared by a process in which polytetrahydrofuran of the general formula

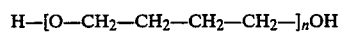

II is reacted with acetylene.

4 Claims, No Drawings

POLYTETRAHYDROFURAN VINYL ETHERS

The present invention relates to novel polytetrahydrofuran vinyl ethers and a process for their preparation.

Polytetrahydrofuran and derivatives of polytetrahydrofuran have attracted a great deal of attention as intermediates for the preparation of polymers. Polytetrahydrofuran derivatives having terminal reactive groups, such as polytetrahydrofuran-$\omega,\omega'$-diamines (U.S. Pat. No. 3,824,198), which permit the incorporation of the polybutanediol chain in polymers, are particularly desirable.

The present invention relates to novel polytetrahydrofuran derivatives which can advantageously be used for the synthesis of polymeric plastics. These novel compounds are of the general formula $$H_2C=HC-[O-CH_2-CH_2-CH_2-CH_2-]_nO-R \qquad I$$

where R is hydrogen or the $CH_2=CH$ radical and n is from 2 to 150, preferably from 3 to 70, in particular from 3 to 55. Among these compounds, the divinyl ethers are of particular industrial interest.

The novel polytetrahydrofuran vinyl ethers of the formula I are prepared by reacting a polytetrahydrofuran of the formula $$H-[O-CH_2-CH_2-CH_2-CH_2-]_nOH \qquad II$$

where n has the abovementioned meaning, with acetylene in the presence of a vinylation catalyst at from 100° to 200° C. and under from 5 to 25 atm.

The reaction of alcohols with acetylene in the presence of strongly basic catalysts has been disclosed as a vinyl reaction by Reppe (cf. Liebigs Ann. Chem. 601 (1956), 81). If the vinylation reaction is applied to relatively long-chain polyhydric alcohols, it is likely that the monovinyl ether initially formed will react with a free hydroxyl group of the same molecule with formation of a cyclic acetaldehyde acetal. It was therefore surprising that, in the novel vinylation, exclusively the vinylated products of formula I are obtained.

The vinylation according to the invention is carried out at from 100° to 200° C., preferably from 50° to 170° C., and under from 5 to 25, preferably from 10 to 25, atm. The catalysts used are conventional vinylation catalysts, in particular strongly basic catalysts, such as alkali metal hydroxides, for example KOH or NaOH, or alkali metal alcoholates, such as sodium methylate, sodium ethylate, potassium methylate or potassium tert-butylate. The catalysts are used, for example, in amounts of from 1 to 10% by weight, based on the polytetrahydrofuran.

For safety reasons, acetylene is preferably diluted with an inert gas, such as nitrogen. The vinylation is carried out in the presence or absence of solvents. Examples of suitable solvents are tetrahydrofuran, dioxane, toluene, decalin, cyclohexane and N-methylpyrrolidone. The novel process can be controlled to give partial or complete vinylation. To achieve complete vinylation of the starting materials to the divinyl ethers, not less than the stoichiometric amount of acetylene is used. The degree of vinylation can be determined exactly by the amount of acetylene used. In the case of partial vinylation, a mixture which contains the starting compound (II), the monovinyl ether (I in which R is —OH) and the divinyl ether (I in which R is —CH=CH$_2$) is obtained. Partial vinylation is advantageously carried out in a hydraulically operated, vertical tube reactor. The reaction temperatures and the catalyst used are the same as in the vinylation in an autoclave. Because of the hydraulic method, for example, it is possible to employ pure acetylene under from 5 to 25, preferably from 12 to 18, atm.

EXAMPLE 1

60 g (1.07 moles) of KOH powder are added to 3 kg (12 moles) of polytetrahydrofuran having a molecular weight of 250 (n=3.22) in an 8 l autoclave. The autoclave is flushed with nitrogen and heated to 160° C. After the reaction temperature (160° C.) has been reached, first 10 atm of nitrogen and then 10 atm of acetylene are forced in. Acetylene is fed in at the rate at which it is consumed. After the end of the reaction (about 24 hours), the discharged mixture is distilled. At a maximum distillation temperature of 155° C. and under 0.3 bar, 3.3 kg of vinylated polytetrahydrofuran containing >95% by weight of polytetrahydrofuran divinyl ether (cf. formula I where R is —CH=CH$_2$ and n is 3.22) are obtained.

Analysis: 1—NMR (CDCl$_3$, 250 MHz): $\delta=1.16$ (m, 14.2H), 3.4 (m, 9.8H), 3.7 (t, 4H), 4.0 (m, 2H), 4.2 (m, 2H), 6.4 (dd, 2H), OH number 12.

EXAMPLE 2

Polytetrahydrofuran having a molecular weight of 1,000 (n =13.64) is mixed with tetrahydrofuran in a ratio of 1:1. 0.5 l/h of the solution thus obtained is passed, at 150° C. and under an acetylene pressure of 18 atm, into a hydraulically operated, vertical 3 l tube reactor. At the same time, 100 ml/h of a 5% strength solution of KOH in a mixture of equal amounts by weight of polytetrahydrofuran and tetrahydrofuran are introduced into the reactor via a second feed. The degree of vinylation of the products obtained in this reaction is from 1 to 98%, depending on the amount of acetylene. With an acetylene feed of 60 l/h, a degree of vinylation of 12% is obtained. The OH number of the resulting product is 99. At an acetylene feed of 110 l/h, a degree of vinylation of 55% is obtained. The OH number of the resulting product is 50.

We claim:

1. A polytetrahydrofuran vinyl ether of the formula $$H_2C=HC-[O-CH_2-CH_2-CH_2-CH_2-]_nO-R \qquad I$$

where R is hydrogen or the $CH_2=CH$ radical and n is from 2 to 150.

2. A polytetrahydrofuran ether as claimed in claim 1, wherein R is the $CH_2=CH$ radical.

3. A polytetrahydrofuran ether as claimed in claim 1, wherein n is 3 to 70.

4. A polytetrahydrofuran ether as claimed in claim 1, wherein n is 3 to 55.

UNITED STATES PATENT AND TRADEMARK OFFICE
CERTIFICATE OF CORRECTION

PATENT NO. : 4,967,015
DATED : October 30, 1990
INVENTOR(S) : Michael Karcher, Heinz Eckhardt and Jochem Henkelmann It is certified that error appears in the above-identified patent and that said Letters Patent is hereby corrected as shown below:

ON THE TITLE PAGE IN THE ABSTRACT:

Please correct formula I to read as follows

-- $H_2C=HC-[O-CH_2-CH_2-CH_2-CH_2-]_nO-R$ --.

IN THE CLAIMS:

Claim 1: please correct formula I to read as follows:

-- $H_2C=HC-[O-CH_2-CH_2-CH_2-CH_2-]_nO-R$ --

Signed and Sealed this

Third Day of March, 1992

*Attest:*

HARRY F. MANBECK, JR.

*Attesting Officer*    Commissioner of Patents and Trademarks